US00PP34142P2

(12) United States Plant Patent
Trees

(10) Patent No.: US PP34,142 P2
(45) Date of Patent: Apr. 19, 2022

(54) ***BUDDLEIA* PLANT NAMED 'CONBUD2080'**

(50) Latin Name: *Buddleia davidii*
Varietal Denomination: Conbud2080

(71) Applicant: The Conard Pyle Company, West Grove, PA (US)

(72) Inventor: Scott C. Trees, Arroyo Grande, CA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/482,954

(22) Filed: Sep. 23, 2021

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 6/00; A01H 5/02
See application file for complete search history.

(56) References Cited

U.S. PATENT DOCUMENTS

PP25,730 P2 7/2015 Trees

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, referred to by its cultivar name, 'Conbud2080', is disclosed. The new variety displays purple-rose colored flowers and dark green colored foliage. Attractive moderately vigorous vegetative is formed. The growth habit is compact and well-branched. The new variety is well suited for providing attractive ornamentation in the landscape.

2 Drawing Sheets

Latin name of genus and species of plant claimed: *Buddleia davidii.*

Variety denomination: 'Conbud2080'.

BACKGROUND OF THE INVENTION

The new variety of *Buddleia davidii* plant originated in a controlled breeding program in Guadalupe, Calif. during June 2016. The objective of the breeding program was the development of a series of *Buddleia* cultivars with compact and well-branched habits. The new cultivar was created by cross-pollination wherein two parents were crossed which previously had been studied in the hope that they would contribute the desired characteristics. The female parent (i.e., the seed parent) was an unnamed breeder seedling variety (not patented). The male parent (i.e., the pollen parent) was a different unnamed breeder seedling variety (not patented).

The parentage of the new variety can be summarized as follows:

unnamed breeder seedling x different unnamed breeder seedling

The new cultivar was discovered and selected as a single flowering plant from the progeny resulting from the above-stated cross-pollination during July 2017 in a controlled environment in Guadalupe, Calif. Selective study resulted in the identification of a single plant of the new variety.

The new variety has been found to undergo asexual propagation by terminal stem cuttings. Asexual propagation by terminal stem cuttings in Guadalupe, Calif. since August 2017 has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Buddleia* plant of the present invention:

(a) forms purple-rose colored flowers,
(b) displays dark green colored foliage, and
(c) exhibits a moderately vigorous, compact, and well-branched growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the female parent unnamed breeding seedling (i.e., the seed parent) displays grey-sliver colored foliage and medium lavender colored flowers, whereas the new variety provides dark green colored foliage and purple-rose colored flowers. The male parent which is a different unnamed breeder seedling (i.e., the pollen parent) displays medium green colored foliage and dark purple-violet colored flowers, whereas the new variety displays dark green colored foliage and purple-rose colored flowers.

The new variety can also be distinguished from other similar varieties that are commercially available. For instance, the new variety of the present invention can readily be distinguished from the 'Boscranz' variety (U.S. Plant Pat. No. 25,730), as the new cultivar displays a more compact growth habit, as compared to plants of the 'Boscranz' variety. In addition, the 'Boscranz' variety forms dark cranberry colored flowers, whereas the new variety forms purple-rose colored flowers.

The new variety has been named 'Conbud2080'.

The new variety was first sold in April 2021 by the inventor or by another who obtained the new variety directly or indirectly from the inventor.

BRIEF DESCRIPTION OF THE PHOTOGRAPH

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Conbud2080' variety. The plants were grown in three-gallon pots for approximately one year outside at Cochranville, Pa. Plants were pinched once after transplant. Photographs were taken in August 2018.

DETAILED BOTANICAL DESCRIPTION

Figure 1:
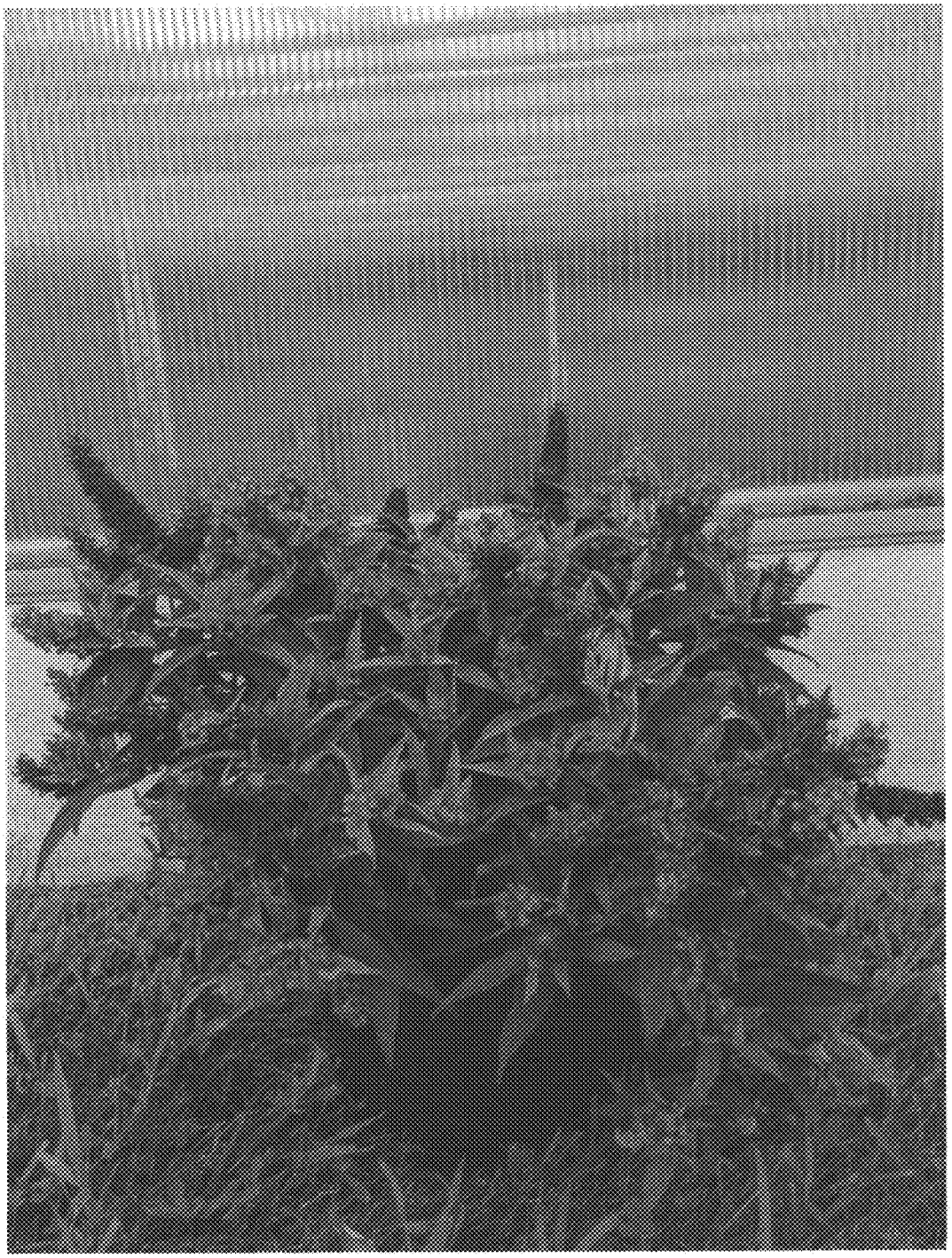
FIG. 1 illustrates a specimen of the plant displaying the overall growth and flowering habit—side view.
Figure 2:
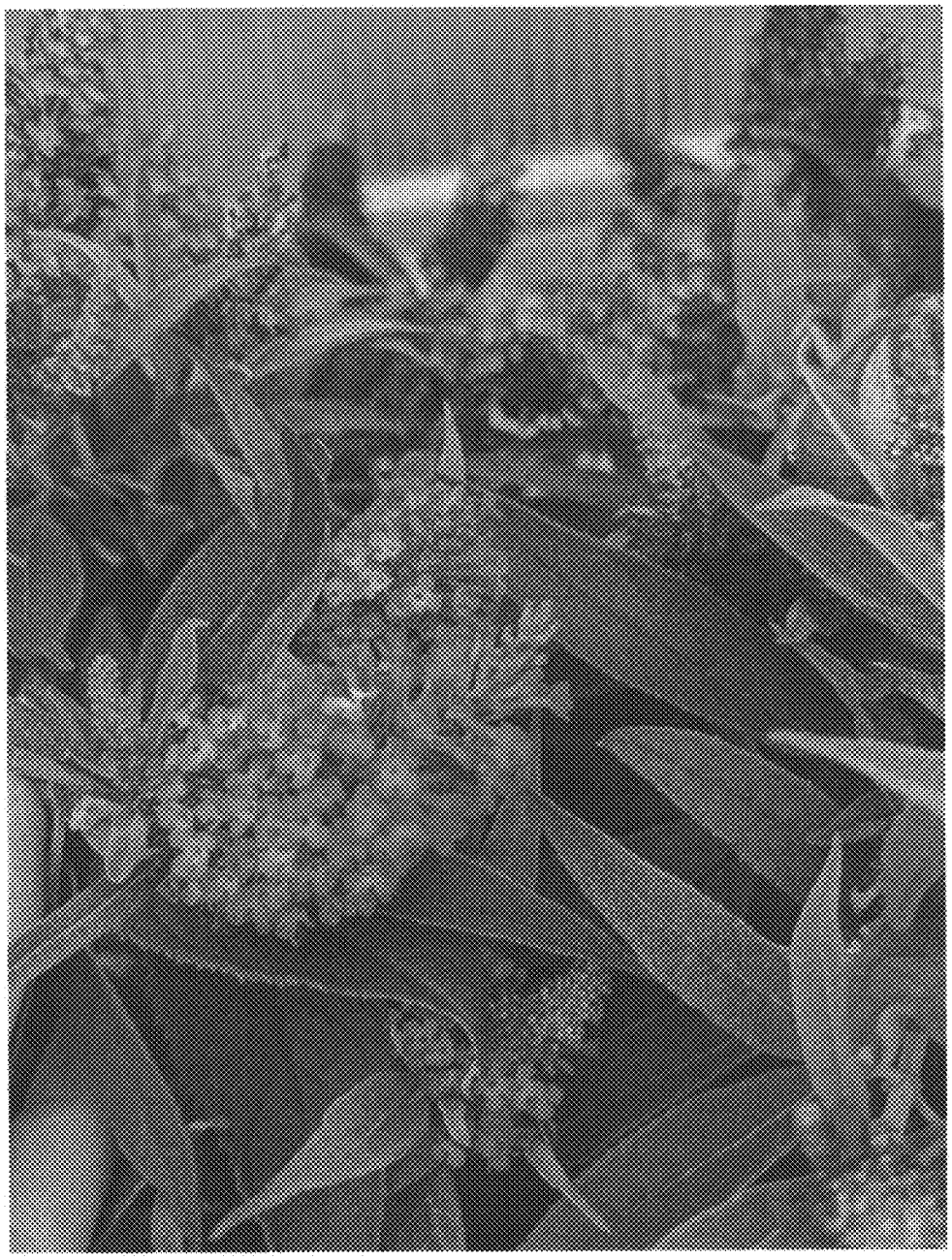
FIG. 2 illustrates a specimen of an inflorescence—close-up view.

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in July 2021 under natural light conditions in Cochranville, Pa. The description is based on the observation of plants produced from cuttings from stock plants and grown in three-gallon containers for approximately one year in an outdoor nursery in Cochranville, Pa. Plants were pinched once after transplant.

Propagation:

*Type cutting.*—Terminal stem.

*Time to initiate roots.*—Approximately 10 to 14 days on average.

*Time to produce a rooted cutting.*—Approximately 21 to 25 days on average.

*Root description.*—Fibrous.

*Rooting habit.*—Freely branching.

Plant:

*Habit.*—Moderately vigorous, compact, and well-branched growth habit.

*Commercial crop time.*—Approximately 2 months from a rooted cutting to finish in a 3-gallon container on average.

*Size.*—Approximately 28.0 cm in height from soil level to top of plant plane on average; and approximately 43.0 cm in width on average.

Branches:

*Branching habit.*—Freely branching, pinching enhances basal branching.

*Quantity of main branches per plant.*—Approximately 8 on average.

*Strength.*—Commonly strong, somewhat flexible, and becomes woody with age.

*Size.*—Length: approximately 22.0 cm on average. — diameter: approximately 4.0 mm on average. — length of central internode: approximately 5.0 cm on average.

*Texture.*—Viscid, densely glandular pubescent.

*Color.*—Young stems: commonly near Yellow-Green Group 146C with some coloring of near Brown Group 200B. — mature stems: commonly near Greyed-Orange Group 177C.

*Number of leaves.*—Approximately 30 per branch on average; and approximately 10 per branched lateral stem on average.

*Fragrance.*—None detected.

*Form.*—Simple.

*Arrangement.*—Opposite.

*Durability to stress.*—Moderate to high.

Leaves:

*Aspect.*—Primarily perpendicular to stem.

*Shape.*—General: lanceolate to oblanceolate. — margin: serrulate. — apex: acute. — base: attenuate.

*Venation.*—Pattern: pinnate, reticulate.

*Size.*—Length of mature leaf: approximately 10.5 cm on average. — width of mature leaf: approximately 2.5 cm on average.

*Texture.*—Upper and lower surfaces: pubescent.

*Color.*—Upper surface of mature foliage: commonly between near Green Group 137A and 137B. — lower surface of mature foliage: commonly near Greyed-Green Group 194A.

*Petiole.*—Shape: rounded, slightly curved. — length: approximately 3.0 mm on average. — width: approximately 3.0 mm on average. — texture: densely pubescent with lanulose hairs. — color: commonly near Greyed-Green Group 192B.

Inflorescence:

*Quantity.*—Approximately 18 open inflorescences per plant on average; and approximately 500 flowers per inflorescence opening from base to apex.

*Type.*—Terminal panicles, each panicle having about 2 to 4 branches on average; and flowers persistent, facing upward and outward.

*Shape.*—Conical.

*Fragrance.*—Very faint.

*Depth or height.*—Approximately 10.0 cm on average.

*Width.*—Approximately 3.5 cm on average.

*Rachis.*—Strength: strong. — length: approximately 10.0 cm on average. — diameter: approximately 2.0 mm on average. — texture: pubescent with stellate hairs. — color: commonly near Yellow-Green Group 146B.

Flower:

*Type.*—Single, salverform.

*Bud just before opening.*—Shape: oblong. — length: approximately 6.0 mm on average. — diameter: approximately 1.0 mm on average. — texture: glabrous. — color of petals: commonly near Violet Group 83A.

*Corolla.*—Shape: rotate, commonly 4 petals arranged in a single whorl. — depth: approximately 1.0 cm on average. — width: approximately 8.0 mm on average.

*Petals.*—Shape: rotund. margin: erosulate. apex: rounded. — length from throat: approximately 8.0 mm on average. — width: approximately 3.0 mm on average. — texture of upper and lower surfaces:

glabrous. — color of upper and lower surfaces when first and fully open: commonly near Purple-Violet Group N81A.

*Corolla tube.*—Length: approximately 7.0 mm on average. — width: approximately 1.0 mm on average. — diameter of throat opening: approximately 1.0 mm on average. — inner surface: texture is lightly pubescent and color is commonly near Greyed-Orange Group N163B. — outer surface: texture is glabrous and color is commonly near Red-Purple Group 63B.

*Calyx.*—Shape: tubular. — length: approximately 3.0 mm on average. — diameter: approximately 1.0 mm on average.

*Sepals.*—Quantity per flower: commonly 4 on average, fused at base. — length: approximately 3.0 mm on average. — width: commonly less than 1.0 mm. — apex: acute. — margin of free portion: entire. — inner surface: texture: glabrous. color: commonly near Yellow-Green Group 144C. — outer surface: texture: moderately pubescent. color: commonly near Yellow-Green Group 144C.

*Pedicels.*—Strength: strong, flexible. — length: approximately 3.0 mm on average. — diameter: approximately 1.0 mm on average. — texture: densely pubescent with stellate hairs. — color: commonly near Yellow-Green Group 146C.

*Reproductive organs.*—Androecium: stamen: commonly 4 per flower, completely adnate to corolla. anther: shape is lanceolate; length is approximately 1.0 mm on average; and color is commonly near Yellow Group 13A. pollen: amount is moderate; coloration is commonly near Yellow Group 13C. — gynoecium: pistil: commonly 1 per flower; length is approximately 2.0 mm on average. stigma: shape is cleft, two-parted; length is approximately 1.0 mm on average; color is commonly near Yellow-Green Group 144A. style: length is approximately 1.0 mm; color is commonly near Yellow-Green Group 145B, opaque. ovary: length is approximately 1.5 mm; color is commonly near Yellow-Green Group 145A. — seed and fruit: none have been observed to date.

Development:

*Blooming.*—Freely flowering under outdoor growing conditions with substantially continuous blooming from late spring through mid-fall.

*Lastingness of individual flower.*—Approximately 5 days on average.

*Tolerance to disease and pest.*—Not observed to date.

The new 'Conbud2080' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Buddleia* plant named 'Conbud2080' characterized by the following combination of characteristics:

(a) forms purple-rose colored flowers, (b) displays dark green colored foliage, and (c) exhibits a moderately vigorous, compact, and well-branched growth habit;

substantially as herein shown and described.

* * * * *